United States Patent [19]
Lee

[11] Patent Number: 5,271,944
[45] Date of Patent: Dec. 21, 1993

[54] PHARMACOLOGICALLY ENHANCED FORMULATIONS

[75] Inventor: Sung J. Lee, Clarks Summit, Pa.

[73] Assignee: Biofor, Ltd., Waverly, Pa.

[21] Appl. No.: 680,997

[22] Filed: Apr. 5, 1991

[51] Int. Cl.⁵ .............................................. A61K 9/16
[52] U.S. Cl. .................................. 424/489; 424/468
[58] Field of Search ........................... 424/468, 489; 514/230.8, 53, 122; 544/74

[56] References Cited

U.S. PATENT DOCUMENTS

| | | | |
|---|---|---|---|
| 4,552,874 | 11/1985 | Mardin et al. | 544/74 |
| 4,880,623 | 11/1989 | Piergiorgio | 424/468 |
| 4,892,870 | 1/1990 | Lee | 514/230.8 |
| 4,912,093 | 3/1990 | Michaeli | 514/53 |
| 4,956,366 | 9/1990 | Nimmesgern | 544/122 |

Primary Examiner—Thurman K. Page
Assistant Examiner—William E. Benston, Jr.
Attorney, Agent, or Firm—Joseph W. Molasky & Associates

[57] ABSTRACT

An anti-inflammatory composition in which the active ingredient is micronized to form an intimate admixture which can be administered orally.

8 Claims, No Drawings

PHARMACOLOGICALLY ENHANCED FORMULATIONS

This invention relates to a homogeneous composition in which the pharmacologically active component is present in the form of microparticles or microgranules.

Specifically, the active ingredient of this invention is described in U.S. Pat. No. 4,892,870 where it is identified as dihydro-4-(3,5-di-tert-butyl-4-hydroxy-benzylidene)-2-methyl-2 H-1,2-oxazin-3(4H)-one (Example 2). This compound has been formulated with various excipients and it has been tested over a wide range of concentrations in a variety of unit dosage forms. It is useful in treating the debilitating effects of inflammation and arthritis and, also, it has been found useful as an analgesic agent, an immunomodulating agent and an anti-pyretic agent.

With the addition of this compound to the arsenal of new anti-arthritic drugs efforts have been directed to enhancing bioavailability through new delivery systems; however, a threshold appears to have been reached and attempts at extending or enhancing the therapeutic effectiveness of this compound have had no success.

Accordingly, there is a need for means by which to increase the bioavailability of dihydro-4-(3,5-di-tert-butyl-4-hydroxybenzylidene) -2-methyl-2H-1,2-oxazin-3(4H)-one and thus improve its therapeutic efficiency.

BACKGROUND

In U.S. Pat. No. 4,880,623 R. Piergiorgio describes a solid pharmaceutical formulation in which Nifedipine is combined with polyethylene glycol (PEG) and the mixture is coprecipitated onto a micronized excipient. Alternatively, PEG may be precipitated onto a homogeneous mixture of the micronized Nifedipine and excipient. In either case the object is to exploit the surfactant properties of PEG so that upon drying the coated surfaces repel one another and protect the microparticles from the agglomerating effects which would otherwise occur.

The difficulty with surfacants however is their high molecular weight and their introduction to the system of lipophilic and hydrophilic groups. In principle these groups enhance stability by lowering interfacial tensions; however, in practice they also alter the physicochemical nature of the various interfaces and change the relationship between the active ingredient and other components of the composition.

In U.S. Pat. No. 4,938,962 M. Trebosc describes a topical formulation in which vitamin E and microparticles of a caffeine metal carboxylate are combined with an insoluble hydroalcoholic gel. The object is to provide a heterogenous cosmetic with slow-release capabilities for use as a slenderizer in treating cellulitis. The micronized particles are released from the gel slowly over a period of time and the insolubility of the active ingredient in the carrier ensures product efficacy.

Although Trebosc improves on topically administered formulations his procedure has no relevance to compositions in which the active ingredient is administered orally for immediate release.

THE INVENTION

This invention overcomes difficulties associated with known systems by providing compositions in which the active ingredient, that is, dihydro-4-(3,5-di-tert-butyl-4-hydroxybenzylidene)-2-methyl-2H-1,2-oxazin-3(4H)-one, is present in the form of microparticles or microgranules having a diameter of from about 5-40 microns, preferably, 10-25 microns and, more preferably, 15-20 microns. This ingredient is combined with excipients and/or fillers and the like to form homogeneous compositions which exhibit an enhanced therapeutic effect.

The active ingredient of this invention is obtained synthetically in the form of granules which generally have a diameter of from about 0.3-2 mm. In various studies these granules were pulverized and administered in finely divided form to test animals to provide what was believed to be a more readily assimilable drug: however, this anticipated effectiveness was never realized and, therefore, it was believed that further milling (micronization) would not improve to any significant degree the results obtained with the pulverized compound.

Moreover, Appelgren in U.S. Pat. No. 4,840,799 supports this view. Appelgren states in Column 1, lines 31-33 that there is no predictability between micronization and bioavailability and he adds that to the contrary, "bioavailability cannot always be improved upon... by preparing the compound in very fine particulate form (micronizing)".

Surprisingly, however, the opposite was found to be true. Micronization enhanced profoundly the anti-inflammatory effectiveness of the active ingredient; moreover, the degree of increase attributable to this form of delivery is several times and at least six fold that which was observed with the unmicronized product.

Milling Procedure: The granular product was micronized in a standard pin mill having a through-put range of about 65-90 pounds per hour to ensure minimal dwell time in the milling region. A once-through procedure was usually sufficient.

Milling was conducted in a controlled atmosphere under controlled temperatures to ensure product integrity. A fine impact pin mill manufactured by Alpine was found to be suitable and it provided consistently replicative samples of finely reduced product. This apparatus was equipped with a stud design which accommodated feed sizes of approximately 0.1-0.15 inches including small product batches of approximately 1-2 ounces with nearly total recovery of feed material.

The "Alpine" mill is distributed by Air Engineering Systems, Corp., Mountain top, Pennsylvania 18707.

Although a fine impact pin mill was used, other micronizer systems may also be employed as, for example, a pearl mill, pebble mill or other similar equipment capable of providing a finely micronized product. Alternatively, there may be employed a Sturtevant Micronizer which produces a fine mesh material with fines as small as 0.5 microns. In this system hot air and/or super heated steam is used to propel the beaters.

The "Sturtevant Micronizer" is manufactured by Sturtevant, Inc., Boston, Massachusetts 02122.

In a typical operation the granular form of dihydro-4-(3,5-di-tert-butyl-4-hydroxybenzylidene)-2 -methyl-2H-1,2-oxazin-3(4H)-one form was placed into a pin mill and the product was reduced to a particle size of less than 30 microns as determined by light microscopy. X-ray analysis of the milled product indicated that its crystalline structure remained unchanged.

The micronized product obtained in this manner was used as sample material for conducting the anti-inflammatory, analgesic and polyarthritic studies described with particularity hereinbelow.

EXAMPLE 1

Formulation

Step A: Micronized Sample

The compound, dihydro-4-(3,5-di-tert-butyl-4-hydroxy-benzylidene)-2-methyl-2H-1,2-oxazin-3(4H)-one, in its unmicronized state was X-ray analyzed and its crystalline pattern was observed.

This sample was placed in a pin mill (Fine Impact Mill, 100 UPZ; Alpine Laboratory Model) and subjected to particle size reduction at a speed setting of 60%.

The particle size of this milled sample was in the range of 10–20 microns as determined by light microscopy. X-ray analysis confirmed that there was no visible change in crystalline structure as a result of the milling procedure.

Step B: Pulverized Sample

The unmicronized compound of Step A was pulverized by hand with a mortar and pestle for 10 minutes. The resulting fine powder had a particle size which was the finest that could be obtained by hand.

The effect of particle size on pharmacological activity was determined by orally administering identical doses of the samples obtained according to Steps A and B to test animals in standard studies. The results of this investigation are presented in the following embodiments.

EXAMPLE 2

Analgesic Activity

This study was performed to evaluate and compare the analgesic effectiveness of the micronized and pulverized samples described in Example 1, Step A and Example 1, Step B. Analgesic activity was evaluated via the mouse acetylcholine writhing test using a modification of the procedure described by Collier et al in Nature (New Biol.), Volume 204: page 1316 (1964) and the British Journal of Pharmacology, Chemotherapy, Volume 32: page 295 (1968).

The test groups consisted of ten mile CD-1 mice (Charles River Laboratories) weighing 18–28 grams each. Test compounds suspended in 0.25% methylcellulose solution were administered orally by gavage and four hours later the mice were injected intraperitoneally with acetylcholine (0.55 mg/ml in 0.25% methyl cellulose). The number of writhes in each group of mice were counted for 10 minutes immediately following the injection of acetylcholine and percent inhibition was calculated as follows:

TABLE I

| ACETYLCHOLINE WRITHING ASSAY | |
| --- | --- |
| Compounds | % Inhibition |
| Example 1, Step B (1 mg/kg) pulverized | 63 |
| Example 1, Step A (1 mg/kg) micronized | 100 |
| Control | 0 |

$$\text{Inhibition (\%)} = \frac{\text{Total number of writhes in test group}}{\text{Total number of writhes in control group}} \times 100$$

These results show the profound effect which micronization exerts on analgesic effectiveness compared to the pulverized form.

EXAMPLE 3

Anti-Inflammatory Activity

The effectiveness of the micronized sample as an anti-inflammatory agent and its comparison to the pulverized form was evaluated.

This study is a modification of the method described by Wong, et al in the Journal of Pharmacology and Experimental Therapeutics, Vol. 185: No. 1, pages 127–138 (1973).

The left and right rear paws of female Lewis rats (Charles River Laboratories) weighing 160–180 grams each were measured by mercury displacement prior to injection (Day Zero).

Adjuvant arthritis was induced in this rat colony by subcutaneous injection of *Mycobacterium butyricum* (0.75 mg in 0.1 ml light mineral oil, Fisher) using an automated Cornwall syringe. On days 11–15 post-adjuvant, the injected animals with 0.25 to 0.76 ml paw edema were selected and distributed evenly, according to edema size, into control and experimental groups of ten rats each. Vehicle control and drug treatments were assigned to the groups at random. The assay was performed using 1 milligram per kilogran per day of the test compound in a 0.25% methylcellulose vehicle. All animals were dosed once daily for 4 days and on the fifth day both hind paw volumes were again measured using mercury displacement.

The hind paw edema was determined for each rat by subtracting the hind paw volume measured on Day Zero from the hind paw volume measured on the fifth day of the study. Group means were determined and the drug effect was calculated as percent inhibition of the hind paw edema according to the following equation:

TABLE II

| ANTI-INFLAMMATORY ACTIVITY | |
| --- | --- |
| Compounds | % Inhibition |
| Example 1, Step B (1 mg/kg) pulverized | 20 |
| Example 1, Step B (1 mg/kg) micronized | 35 |
| Control | 0 |

$$\% \text{ Inhibition} = \frac{(\text{Mean Control Edema} - \text{Mean Experimental Edema})}{\text{Control Edema}} \times 100$$

These studies show an enhanced anti-inflammatory effect for the micronized sample when compared to the pulverized form.

EXAMPLE 4

Adjuvant Polyarthritis

The object of this study was to compare the anti-inflammatory activity of the micronized and unmicronized samples when administered orally to polyarthritic injected rats.

This anti-inflammatory study was conducted according to the method described by Chang, Y., Pearson, C.M. and Abe, C. in Arthritis and Rheumatism, Volume 23: pp. 62–71 (1980).

Male Lewis rats weighing 200 to 220 grams were divided into groups of 5 and housed in hanging cages with food and water ad libitum. On Day Zero they were injected with 7.5 mg of N,N-dioctadecyl-N',N'bis(2-hydroxyethyl)propane diamine suspended in mineral oil subcutaneously at the base of the tail. On Day 9 the animals were weighed and compound administration was begun. The micronized and unmicronized samples described in Example 1, Steps A and B, were suspended in solution using a tissue homogenizer in 1% carboxy methyl cellulose. These compounds were administered orally once daily for 5 days (Days 9-13) with no dosing on day 14. On Day 15, the hind feet were removed just above the ankle joint and weighed, and percent difference from the diseased control was calculated.

TABLE III

| ADJUVANT POLYARTHRITIS | |
| --- | --- |
| Compounds | $ED_{50}$ (mg/kg) |
| Example 1, Step B (unmicronized) | 16.2 |
| Example 1, Step A (micronized) | 2.8 |

The micronized sample exhibited an almost six fold increase in potency compared to the unmicronized sample.

This invention has been described by reference to precise embodiments but it will be appreciated by those skilled in the art that this invention is subject to various modifications and to the extent that those modifications would be obvious to one of ordinary skill they are considered as being within the scope of the appended claims.

What is claimed is:

1. A pharmaceutical composition comprising as an active ingredient a compound of the formula:

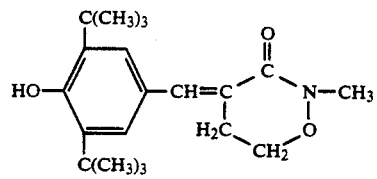

in the form of microparticles having a diameter of between about 5-40 microns, said microparticles being uniformly distributed with the composition components.

2. The composition according to claim 1 wherein the active ingredient is combined with an excipient to provide a formulation suitable for oral administration.

3. The composition according to claim 2 wherein the active ingredient and excipient are homogeneously blended.

4. The composition according to claim 1 wherein the microparticles have a diameter size of between about 10-25 microns.

5. The composition according to claim 1 wherein the microparticles have a diameter size of between about 15-20 microns.

6. The composition according to claim 2 wherein the excipient is a disaccharide.

7. The composition according to claim 6 wherein the excipient is lactose.

8. The composition according to claim 1 wherein the composition is administered in tablet form.

* * * * *